(12) United States Patent
Shelton, IV et al.

(10) Patent No.: US 7,354,447 B2
(45) Date of Patent: Apr. 8, 2008

(54) DISPOSABLE LOADING UNIT AND SURGICAL INSTRUMENTS INCLUDING SAME

(75) Inventors: Frederick E. Shelton, IV, New Vienna, OH (US); Leslie M. Fugikawa, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 45 days.

(21) Appl. No.: 11/271,234

(22) Filed: Nov. 10, 2005

(65) Prior Publication Data

US 2007/0102476 A1    May 10, 2007

(51) Int. Cl.
*A61B 17/04*    (2006.01)
(52) U.S. Cl. ............. 606/219; 227/175.1; 227/19; 227/180.1; 606/167
(58) Field of Classification Search ............ 227/180.1, 227/175.1, 19; 606/219, 205, 167, 75, 220, 606/221, 181, 182, 183; 604/19, 20, 22, 604/501
See application file for complete search history.

(56) References Cited

U.S. PATENT DOCUMENTS

| | | | |
|---|---|---|---|
| 2,037,727 A | 4/1936 | Chapelle | |
| 3,269,630 A | 8/1966 | Fleischer | |
| 3,734,207 A | 5/1973 | Fishbein | |
| 3,894,174 A | 7/1975 | Cartun | |
| 3,940,844 A | 3/1976 | Colby et al. | |
| 4,415,112 A | 11/1983 | Green | |
| 4,475,679 A | 10/1984 | Fleury, Jr. | |
| 4,520,817 A | 6/1985 | Green | |
| 4,526,174 A | 7/1985 | Froehlich | |
| 4,605,001 A | 8/1986 | Rothfuss et al. | |
| 4,606,343 A | 8/1986 | Conta et al. | |
| 4,608,981 A | 9/1986 | Rothfuss et al. | |
| 4,709,120 A | 11/1987 | Pearson | |
| 4,869,415 A | 9/1989 | Fox | |
| 4,892,244 A | 1/1990 | Fox et al. | |
| 4,941,623 A | 7/1990 | Pruitt | |
| 4,955,959 A | 9/1990 | Tompkins et al. | |
| 5,027,834 A | 7/1991 | Pruitt | |
| 5,031,814 A | 7/1991 | Tompkins et al. | |
| 5,040,715 A | 8/1991 | Green et al. | |
| 5,065,929 A | 11/1991 | Schulze et al. | |
| 5,080,556 A | 1/1992 | Carreno | |
| 5,104,025 A | 4/1992 | Main et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,156,315 A | 10/1992 | Green et al. | |
| 5,200,280 A | 4/1993 | Karasa | |

(Continued)

FOREIGN PATENT DOCUMENTS

DE    69328576 T2    1/2001

(Continued)

*Primary Examiner*—John Sipos
*Assistant Examiner*—Michelle Lopez
(74) *Attorney, Agent, or Firm*—Kirkpatrick & Lockhart Preston Gates Ellis LLP

(57) ABSTRACT

A disposable loading unit. The disposable loading unit includes a housing assembly, a knife assembly connected to the housing assembly, and an agent cartridge connected to the housing assembly. The agent cartridge houses a medical agent. The disposable loading unit is configured to deliver the medical agent proximate a cutting surface of the knife assembly.

24 Claims, 10 Drawing Sheets

U.S. PATENT DOCUMENTS

| | | |
|---|---|---|
| 5,207,697 A | 5/1993 | Carusillo et al. |
| 5,211,649 A | 5/1993 | Kohler et al. |
| 5,246,156 A | 9/1993 | Rothfuss et al. |
| 5,253,793 A | 10/1993 | Green et al. |
| RE34,519 E | 1/1994 | Fox et al. |
| 5,275,323 A | 1/1994 | Schulze et al. |
| 5,307,976 A | 5/1994 | Olson et al. |
| 5,309,927 A | 5/1994 | Welch |
| 5,318,221 A | 6/1994 | Green et al. |
| 5,332,142 A | 7/1994 | Robinson et al. |
| 5,350,400 A | 9/1994 | Esposito et al. |
| 5,379,933 A | 1/1995 | Green et al. |
| 5,383,880 A | 1/1995 | Hooven |
| 5,389,098 A | 2/1995 | Tsuruta et al. |
| 5,395,033 A | 3/1995 | Byrne et al. |
| 5,397,046 A | 3/1995 | Savage et al. |
| 5,403,312 A | 4/1995 | Yates et al. |
| 5,413,267 A | 5/1995 | Solyntjes et al. |
| 5,413,268 A | 5/1995 | Green et al. |
| 5,415,335 A | 5/1995 | Knodell, Jr. |
| 5,425,745 A | 6/1995 | Green et al. |
| 5,431,322 A | 7/1995 | Green et al. |
| 5,433,721 A | 7/1995 | Hooven et al. |
| 5,445,304 A | 8/1995 | Plyley et al. |
| 5,456,401 A | 10/1995 | Green et al. |
| 5,462,215 A | 10/1995 | Viola et al. |
| 5,465,895 A | 11/1995 | Knodel et al. |
| 5,465,896 A | 11/1995 | Allen et al. |
| 5,470,006 A | 11/1995 | Rodak |
| 5,472,132 A | 12/1995 | Savage et al. |
| 5,474,566 A | 12/1995 | Alesi et al. |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,503,320 A | 4/1996 | Webster et al. |
| 5,503,638 A | 4/1996 | Cooper et al. |
| 5,509,596 A | 4/1996 | Green et al. |
| 5,518,163 A | 5/1996 | Hooven |
| 5,518,164 A | 5/1996 | Hooven |
| 5,522,817 A | 6/1996 | Sander et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,549,628 A | 8/1996 | Cooper et al. |
| 5,553,675 A | 9/1996 | Pitzen et al. |
| 5,554,169 A | 9/1996 | Green et al. |
| 5,562,239 A | 10/1996 | Boiarski et al. |
| 5,562,241 A | 10/1996 | Knodel et al. |
| 5,574,431 A | 11/1996 | McKeown et al. |
| 5,575,803 A | 11/1996 | Cooper et al. |
| 5,582,611 A | 12/1996 | Tsuruta et al. |
| 5,584,425 A | 12/1996 | Savage et al. |
| 5,586,711 A | 12/1996 | Plyley et al. |
| 5,628,446 A | 5/1997 | Geiste et al. |
| 5,632,432 A | 5/1997 | Schulze et al. |
| 5,636,779 A | 6/1997 | Palmer |
| 5,651,491 A | 7/1997 | Heaton et al. |
| 5,653,374 A | 8/1997 | Young et al. |
| 5,662,258 A | 9/1997 | Knodel et al. |
| 5,667,517 A | 9/1997 | Hooven |
| 5,673,840 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,693,042 A | 12/1997 | Boiarski et al. |
| 5,702,408 A | 12/1997 | Wales et al. |
| 5,704,534 A | 1/1998 | Huitema et al. |
| 5,706,998 A | 1/1998 | Plyley et al. |
| 5,709,680 A | 1/1998 | Yates et al. |
| 5,713,505 A | 2/1998 | Huitema |
| 5,715,988 A | 2/1998 | Palmer |
| 5,718,359 A | 2/1998 | Palmer et al. |
| 5,735,445 A | 4/1998 | Vidal et al. |
| 5,747,953 A | 5/1998 | Philipp |
| 5,752,644 A | 5/1998 | Bolanos et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,796,188 A | 8/1998 | Bays |
| 5,797,537 A | 8/1998 | Oberlin et al. |
| 5,797,538 A | 8/1998 | Heaton et al. |
| 5,807,393 A | 9/1998 | Williamson, IV et al. |
| 5,817,093 A | 10/1998 | Williamson, IV et al. |
| 5,823,066 A | 10/1998 | Huitema et al. |
| 5,826,776 A | 10/1998 | Schulze et al. |
| 5,833,690 A | 11/1998 | Yates et al. |
| 5,843,132 A | 12/1998 | Ilvento |
| 5,865,361 A | 2/1999 | Milliman et al. |
| 5,878,938 A | 3/1999 | Bittner et al. |
| 5,893,506 A | 4/1999 | Powell |
| 5,894,979 A | 4/1999 | Powell |
| 5,911,353 A | 6/1999 | Bolanos et al. |
| 5,918,791 A | 7/1999 | Sorrentino et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,032,849 A | 3/2000 | Mastri et al. |
| 6,079,606 A | 6/2000 | Milliman et al. |
| 6,083,234 A | 7/2000 | Nicholas et al. |
| 6,109,500 A | 8/2000 | Alli et al. |
| H1904 H | 10/2000 | Yates et al. |
| 6,126,670 A | 10/2000 | Walker et al. |
| 6,131,789 A | 10/2000 | Schulze et al. |
| 6,155,473 A | 12/2000 | Tompkins et al. |
| 6,156,056 A | 12/2000 | Kearns et al. |
| 6,202,914 B1 | 3/2001 | Geiste et al. |
| 6,223,835 B1 | 5/2001 | Habedank et al. |
| 6,241,139 B1 | 6/2001 | Milliman et al. |
| 6,250,532 B1 | 6/2001 | Green et al. |
| 6,264,087 B1 | 7/2001 | Whitman |
| 6,273,897 B1 | 8/2001 | Dalessandro et al. |
| 6,315,184 B1 | 11/2001 | Whitman |
| 6,320,123 B1 | 11/2001 | Reimers |
| 6,325,810 B1 | 12/2001 | Hamilton et al. |
| 6,330,965 B1 | 12/2001 | Milliman et al. |
| 6,358,224 B1 | 3/2002 | Tims et al. |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,503,257 B2 | 1/2003 | Grant et al. |
| 6,522,101 B2 | 2/2003 | Malackowski |
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,979 B2 | 1/2004 | Whitman |
| 6,695,199 B2 | 2/2004 | Whitman |

| | | |
|---|---|---|
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,817,509 B2 | 11/2004 | Geiste et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,818 B2 | 2/2006 | Shelton, IV et al. |
| 7,032,798 B2 | 4/2006 | Whitman et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,066,944 B2 | 6/2006 | Laufer et al. |
| 7,077,856 B2 | 7/2006 | Whitman |
| 7,083,075 B2 | 8/2006 | Swayze et al. |
| 7,090,684 B2 | 8/2006 | McGuckin, Jr. et al. |
| 7,098,794 B2 | 8/2006 | Lindsay et al. |
| 7,111,769 B2 | 9/2006 | Wales et al. |
| 7,140,527 B2 | 11/2006 | Ehrenfels et al. |
| 2003/0105478 A1 | 6/2003 | Whitman et al. |
| 2003/0130677 A1 | 7/2003 | Whitman et al. |
| 2003/0216778 A1 | 11/2003 | Weadock |
| 2004/0028502 A1 | 2/2004 | Cummins |
| 2004/0094597 A1 | 5/2004 | Whitman et al. |
| 2004/0097987 A1 | 5/2004 | Pugsley et al. |
| 2004/0111081 A1 | 6/2004 | Whitman et al. |
| 2004/0122471 A1 | 6/2004 | Toby et al. |
| 2004/0167572 A1 | 8/2004 | Roth et al. |
| 2004/0222268 A1 | 11/2004 | Bilotti et al. |
| 2004/0232196 A1 | 11/2004 | Shelton, IV et al. |
| 2004/0232199 A1 | 11/2004 | Shelton, IV et al. |
| 2004/0243151 A1 | 12/2004 | Demmy et al. |
| 2004/0243176 A1 | 12/2004 | Hahnen et al. |
| 2005/0006434 A1 | 1/2005 | Wales et al. |
| 2005/0021026 A1 | 1/2005 | Baily |
| 2005/0070958 A1 | 3/2005 | Swayze et al. |
| 2005/0072827 A1 | 4/2005 | Mollenauer |
| 2005/0107824 A1 | 5/2005 | Hillstead et al. |
| 2005/0119669 A1 | 6/2005 | Demmy |
| 2005/0131390 A1 | 6/2005 | Heinrich et al. |
| 2005/0143759 A1 | 6/2005 | Kelly |
| 2005/0165415 A1 | 7/2005 | Wales |
| 2005/0173490 A1 | 8/2005 | Shelton, IV |
| 2005/0187576 A1 | 8/2005 | Whitman et al. |
| 2005/0189397 A1 | 9/2005 | Jankowski |
| 2005/0203550 A1 | 9/2005 | Laufer et al. |
| 2005/0216055 A1 | 9/2005 | Scirica et al. |
| 2005/0230453 A1* | 10/2005 | Viola ..................... 227/176.1 |
| 2005/0263562 A1 | 12/2005 | Shelton, IV et al. |
| 2006/0011699 A1 | 1/2006 | Olson et al. |
| 2006/0025813 A1* | 2/2006 | Shelton et al. ............... 606/205 |
| 2006/0025816 A1* | 2/2006 | Shelton, IV ................ 606/215 |
| 2006/0087442 A1 | 4/2006 | Smith et al. |
| 2006/0100643 A1 | 5/2006 | Laufer et al. |
| 2006/0122636 A1 | 6/2006 | Bailley et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2007/0034668 A1 | 2/2007 | Holsten et al. |

FOREIGN PATENT DOCUMENTS

| | | |
|---|---|---|
| EP | 0122046 A1 | 10/1984 |
| EP | 0639349 A2 | 2/1994 |
| EP | 0630612 A1 | 12/1994 |
| EP | 0634144 A1 | 1/1995 |
| EP | 0679367 A2 | 11/1995 |
| EP | 0685204 A1 | 12/1995 |
| EP | 0699418 A1 | 3/1996 |
| EP | 0705571 A1 | 4/1996 |
| EP | 0667119 B1 | 7/1996 |
| EP | 0552423 B1 | 1/1998 |
| EP | 0760230 B1 | 2/1999 |
| EP | 0552050 B1 | 5/2000 |
| EP | 1 086 713 B1 | 3/2001 |
| EP | 1256318 B1 | 5/2001 |
| EP | 1238634 A2 | 9/2002 |
| EP | 0656188 B1 | 1/2003 |
| EP | 0705570 B1 | 4/2004 |
| EP | 1426012 A1 | 6/2004 |
| EP | 1520525 A1 | 4/2005 |
| EP | 1550408 A1 | 7/2005 |
| EP | 1064883 B1 | 8/2005 |
| EP | 1621141 A2 | 2/2006 |
| EP | 1045672 B1 | 8/2006 |
| EP | 1617768 B1 | 8/2006 |
| EP | 1129665 B1 | 11/2006 |
| EP | 1256317 B1 | 12/2006 |
| EP | 1479346 B1 | 1/2007 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002369820 A | 12/2002 |
| JP | 2005103293 A | 4/2005 |
| WO | WO 00/72762 A1 | 12/2000 |
| WO | WO 00/72765 A1 | 12/2000 |
| WO | WO 01/05702 A1 | 1/2001 |
| WO | WO 01/62158 A2 | 8/2001 |
| WO | WO 01/62162 A1 | 8/2001 |
| WO | WO 01/62164 A2 | 8/2001 |
| WO | WO 02/43571 A2 | 6/2002 |
| WO | WO 02/067785 A2 | 9/2002 |
| WO | WO 03/000138 A2 | 1/2003 |
| WO | WO 03/001329 A2 | 1/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/090630 A2 | 11/2003 |
| WO | WO 03/094747 A1 | 11/2003 |
| WO | WO 03/105702 A2 | 12/2003 |
| WO | WO 2004/032763 A2 | 4/2004 |
| WO | WO 2004/096057 A2 | 11/2004 |
| WO | WO 2005/027983 A2 | 3/2005 |

* cited by examiner

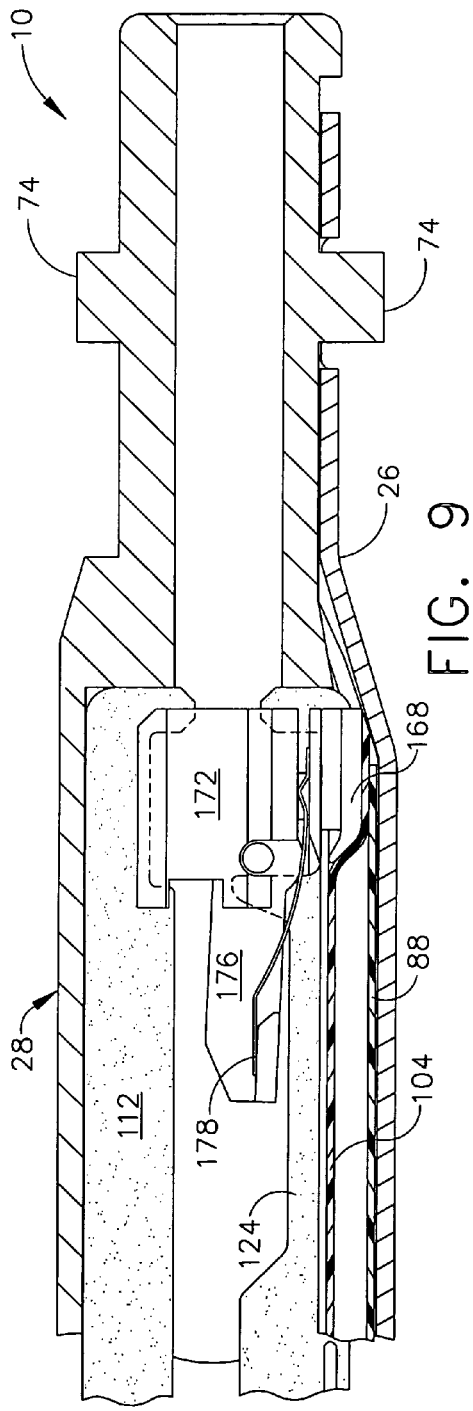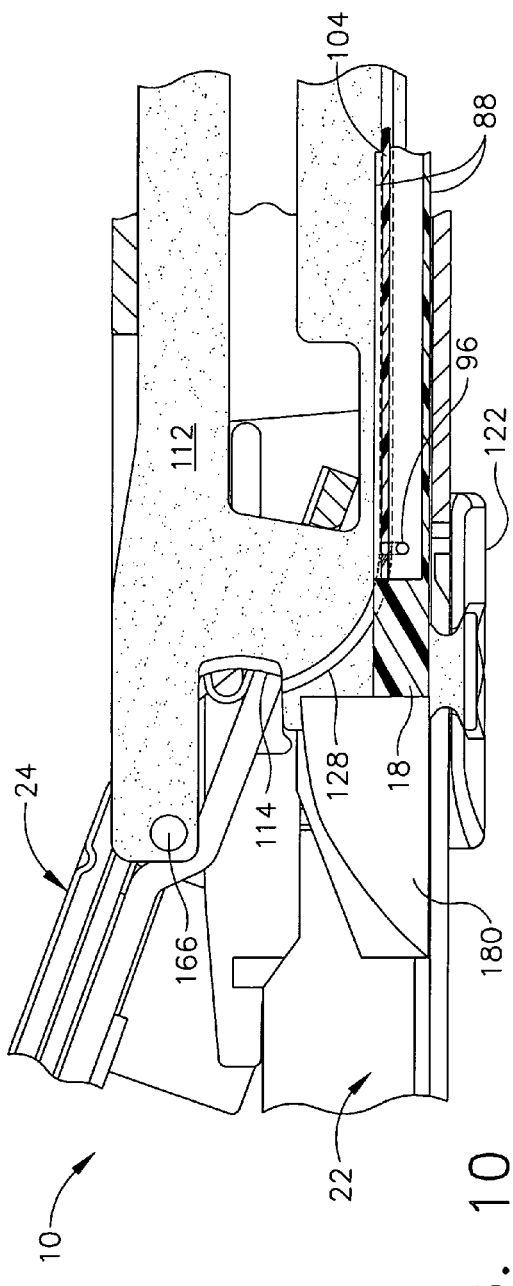

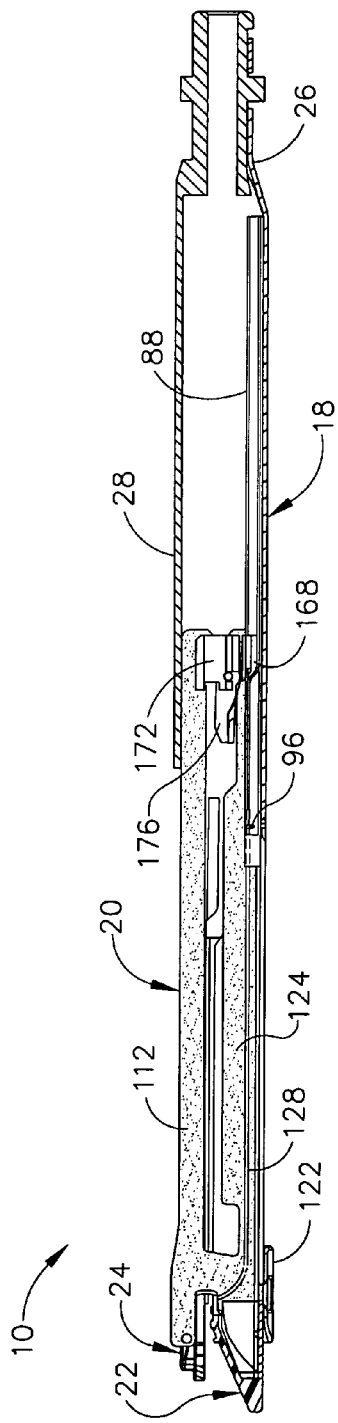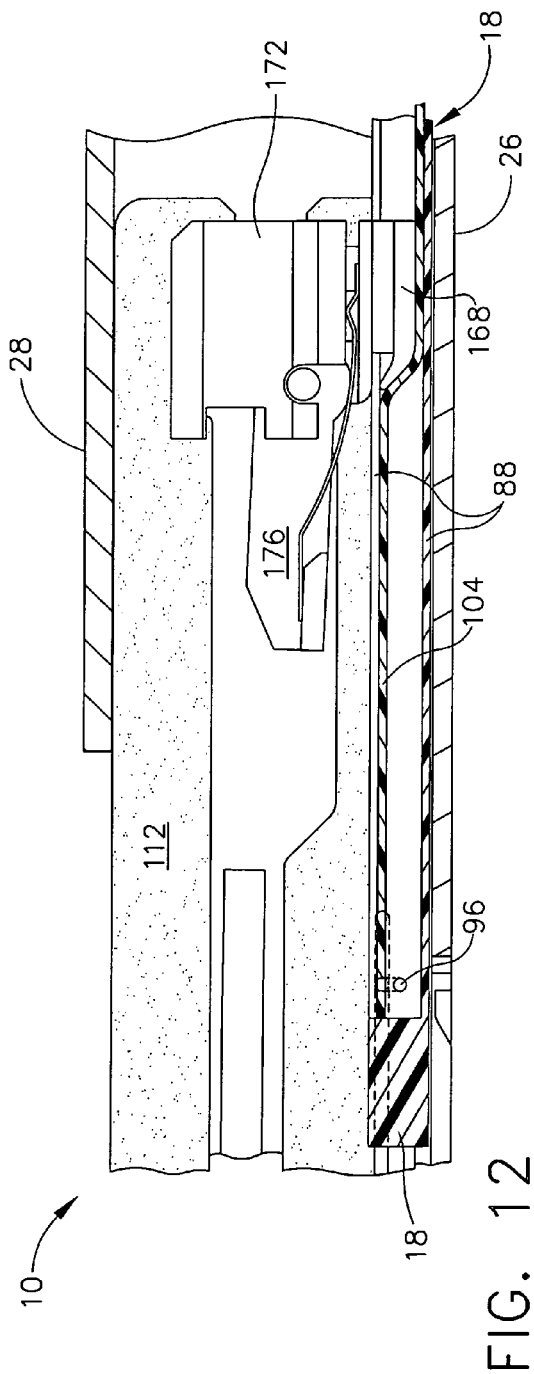

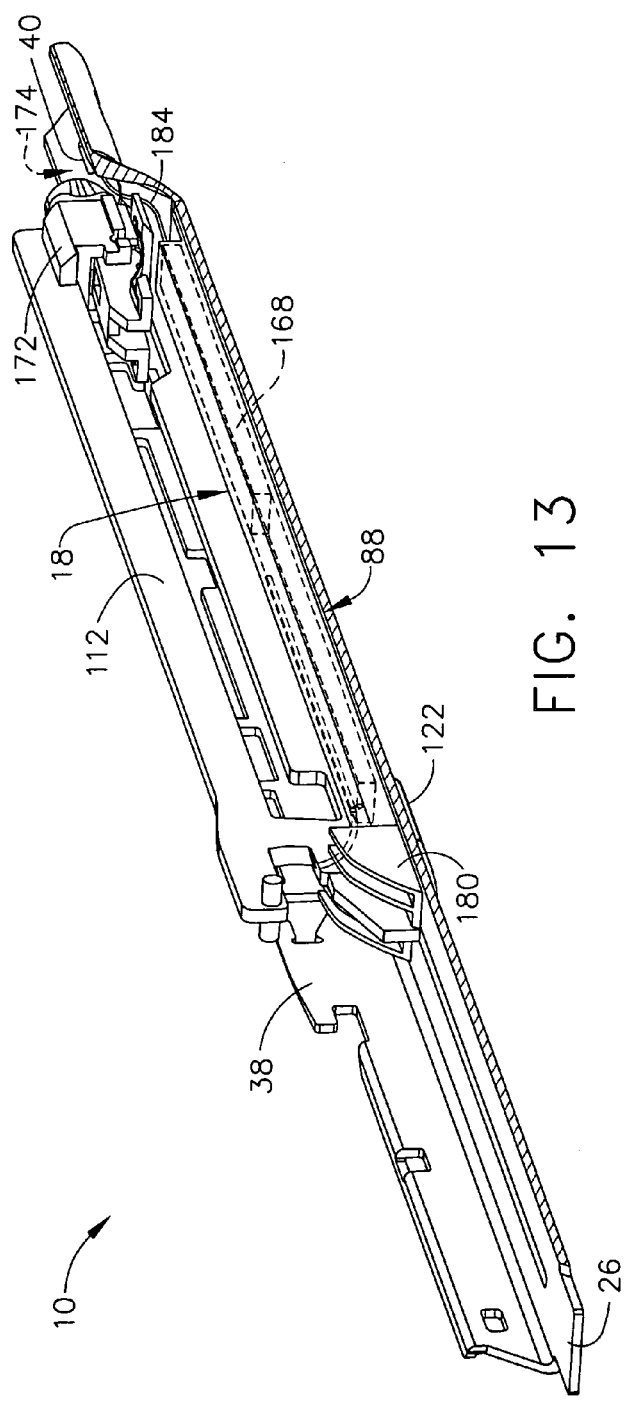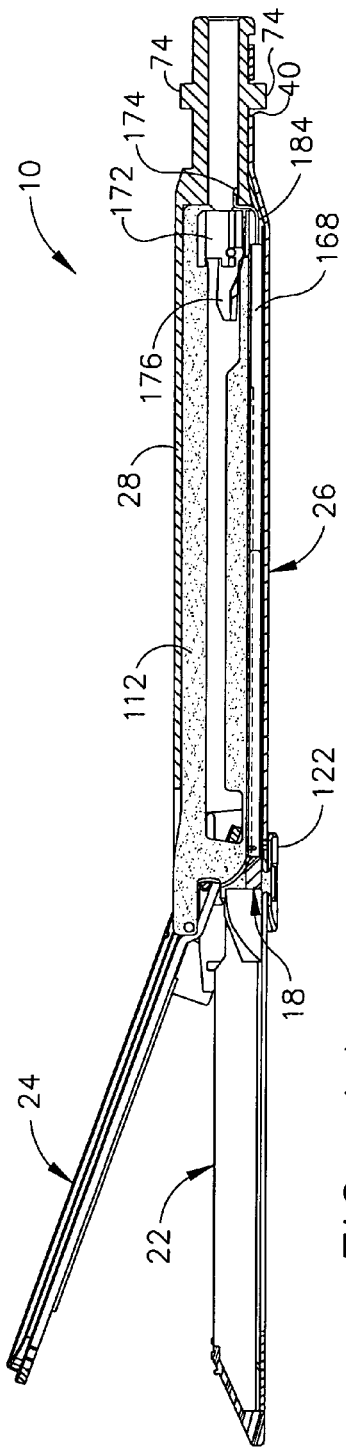
FIG. 13
FIG. 14

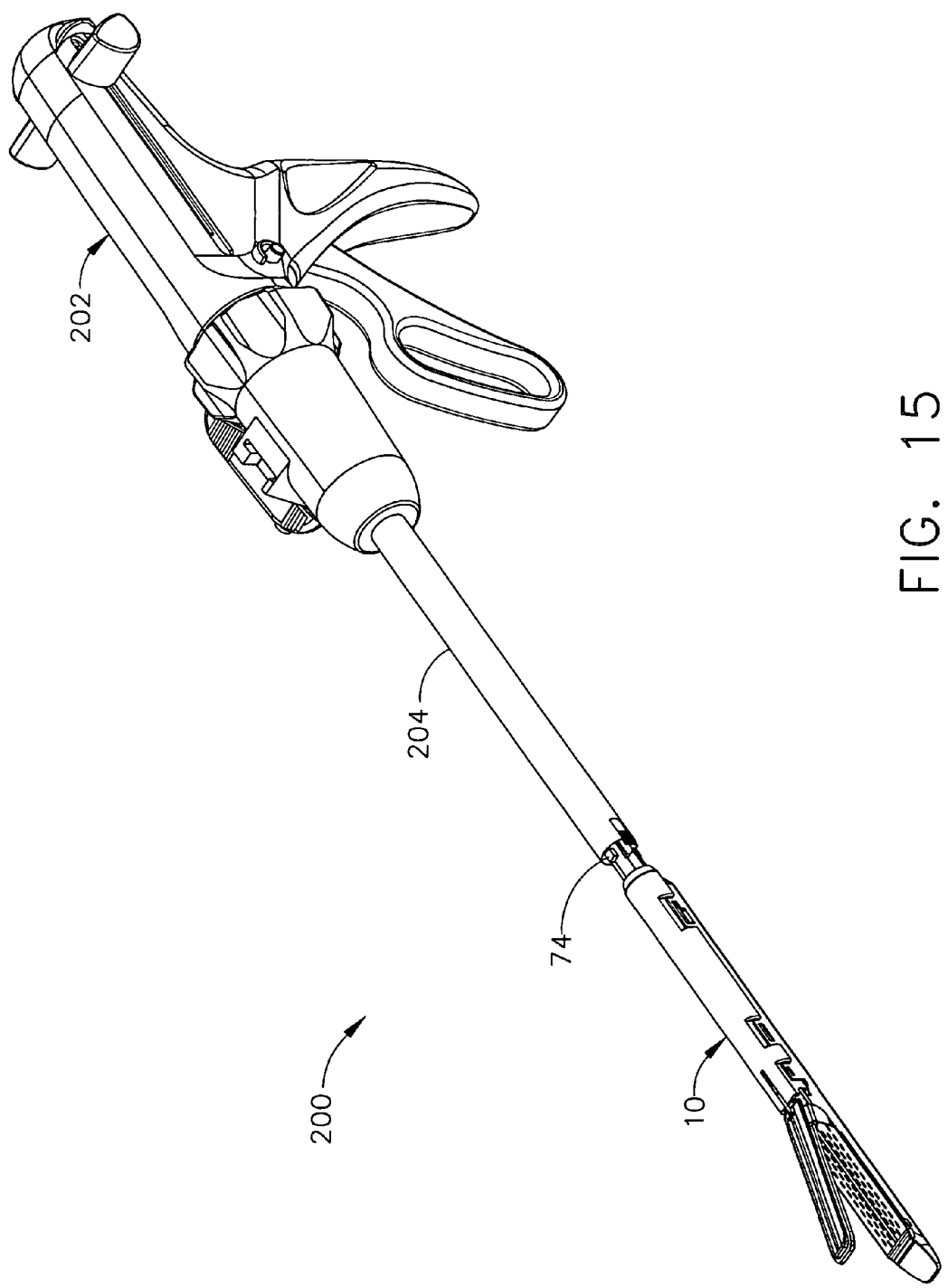

DISPOSABLE LOADING UNIT AND SURGICAL INSTRUMENTS INCLUDING SAME

BACKGROUND OF INVENTION

This application discloses an invention that is related, generally and in various embodiments, to a disposable loading unit configured for connection to a reusable surgical instrument, and to surgical instruments that include a disposable loading unit.

Surgical instruments that are utilized to concurrently make longitudinal incisions in tissue and apply lines of staples on opposing sides of the incisions are known in the art. The tissue may include, for example, human tissue, animal tissue, membranes, or other organic substances. Such surgical instruments commonly include a pair of opposing jaw members that cooperate to grasp or clamp the tissue therebetween and a cutting surface that makes the incision. When employed in endoscopic or laparoscopic applications, the opposing jaw members are capable of passing through a cannula passageway. One of the jaw members typically supports a staple cartridge having at least two laterally spaced rows of staples and pushers aligned with the staples. The other jaw member is movable between an open position and a closed position, and defines an anvil having staple-forming pockets correspondingly aligned with the rows of staples in the staple cartridge. Such instruments may also include a wedge that, when driven, sequentially contacts the pushers to effect the firing of the staples toward the anvil and through the tissue.

The trauma caused to the tissue with such actions can be significant. In general, the delivery of sufficient amounts of medical agents to the site of the traumatized tissue promotes the proper sealing of the incision, reduces the possibility of infection, and/or significantly improves the healing process. The application of medical agents to the site of the traumatized tissue is often accomplished by means other than the surgical instrument that makes the incision and applies the staples. Such means generally increase the complexity and cost associated with the procedure. However, such means are often necessary because many of the surgical instruments utilized to concurrently make the incision and apply the staples are not configured to store and deliver sufficient amounts of medical agents to the site of the traumatized tissue, and the delivery of some medical agents to the site of the traumatized tissue via the surgical instrument would render the surgical instrument unsuitable for reuse.

SUMMARY

In one general respect, this application discloses a disposable loading unit. According to various embodiments, the disposable loading unit comprises a housing assembly, a knife assembly connected to the housing assembly, and an agent cartridge connected to the housing assembly. The agent cartridge houses a medical agent. The disposable loading unit is configured to deliver the medical agent proximate a cutting surface of the knife assembly. The disposable loading unit may further comprise a staple cartridge connected to the housing assembly, and an anvil assembly connected to the housing assembly.

In another general respect, this application discloses a surgical instrument. According to various embodiments, the surgical instrument comprises a handle assembly, an elongated body connected to the handle assembly, and a disposable loading unit releasably connected to the elongated body. The disposable loading unit comprises a housing assembly, a knife assembly connected to the housing assembly, an agent cartridge connected to the housing assembly, and at least one medical agent driver connected to the knife assembly. The agent cartridge houses a medical agent. The disposable loading unit is configured to deliver the medical agent proximate a cutting surface of the knife assembly. The disposable loading unit may further comprise a staple cartridge connected to the housing assembly, and an anvil assembly connected to the housing assembly.

In another general respect, this application discloses a surgical instrument. According to various embodiments, the surgical instrument comprises a handle assembly, an elongated body connected to the handle assembly, and a disposable loading unit releasably connected to the elongated body. The disposable loading unit comprises a housing assembly, a knife assembly connected to the housing assembly, an agent cartridge connected to the housing assembly, and at least one medical agent driver in contact with the agent cartridge. The agent cartridge houses a medical agent. The at least one medical driver comprises an electrically activated polymer. The disposable loading unit is configured to deliver the medical agent proximate a cutting surface of the knife assembly. The disposable loading unit may further comprise a staple cartridge connected to the housing assembly, and an anvil assembly connected to the housing assembly.

DESCRIPTION OF THE DRAWINGS

FIG. 9 illustrates various embodiments of a disposable loading unit;

FIG. 10 illustrates various embodiments of a disposable loading unit;

FIG. 11 illustrates various embodiments of a disposable loading unit;

FIG. 12 illustrates various embodiments of a disposable loading unit;

FIG. 13 illustrates various embodiments of a disposable loading unit;

FIG. 14 illustrates various embodiments of a disposable loading unit; and

FIG. 15 illustrates various embodiments of a surgical instrument.

DETAILED DESCRIPTION OF THE INVENTION

It is to be understood that the figures and descriptions of the disclosed invention have been simplified to illustrate elements that are relevant for a clear understanding of the disclosed invention, while eliminating, for purposes of clarity, other elements. Those of ordinary skill in the art will recognize, however, that these and other elements may be desirable. However, because such elements are well known in the art, and because they do not facilitate a better understanding of the disclosed invention, a discussion of such elements is not provided herein.

Figure 1:
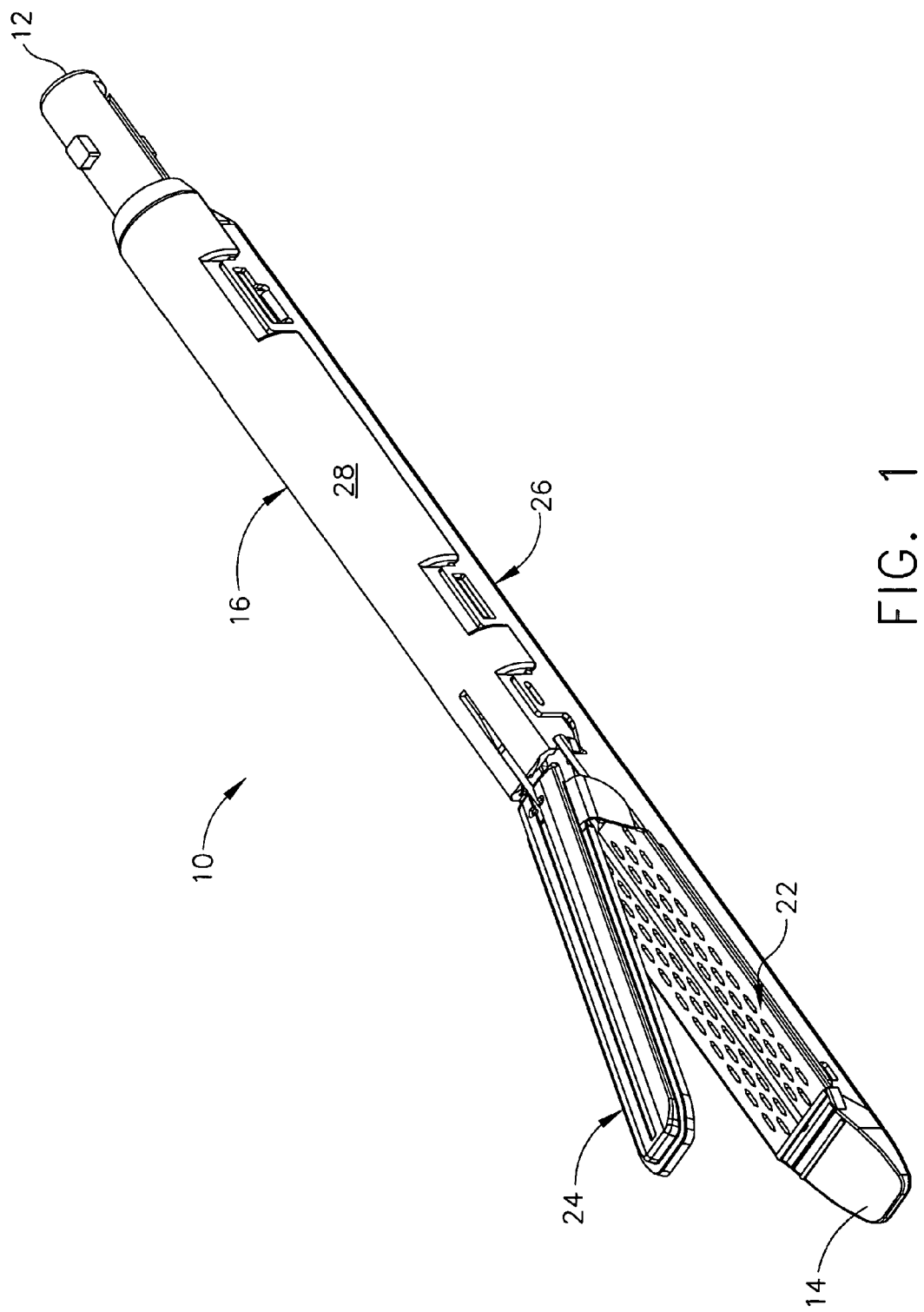
FIGS. 1-2 illustrate various embodiments of a disposable loading unit.
Figure 2:
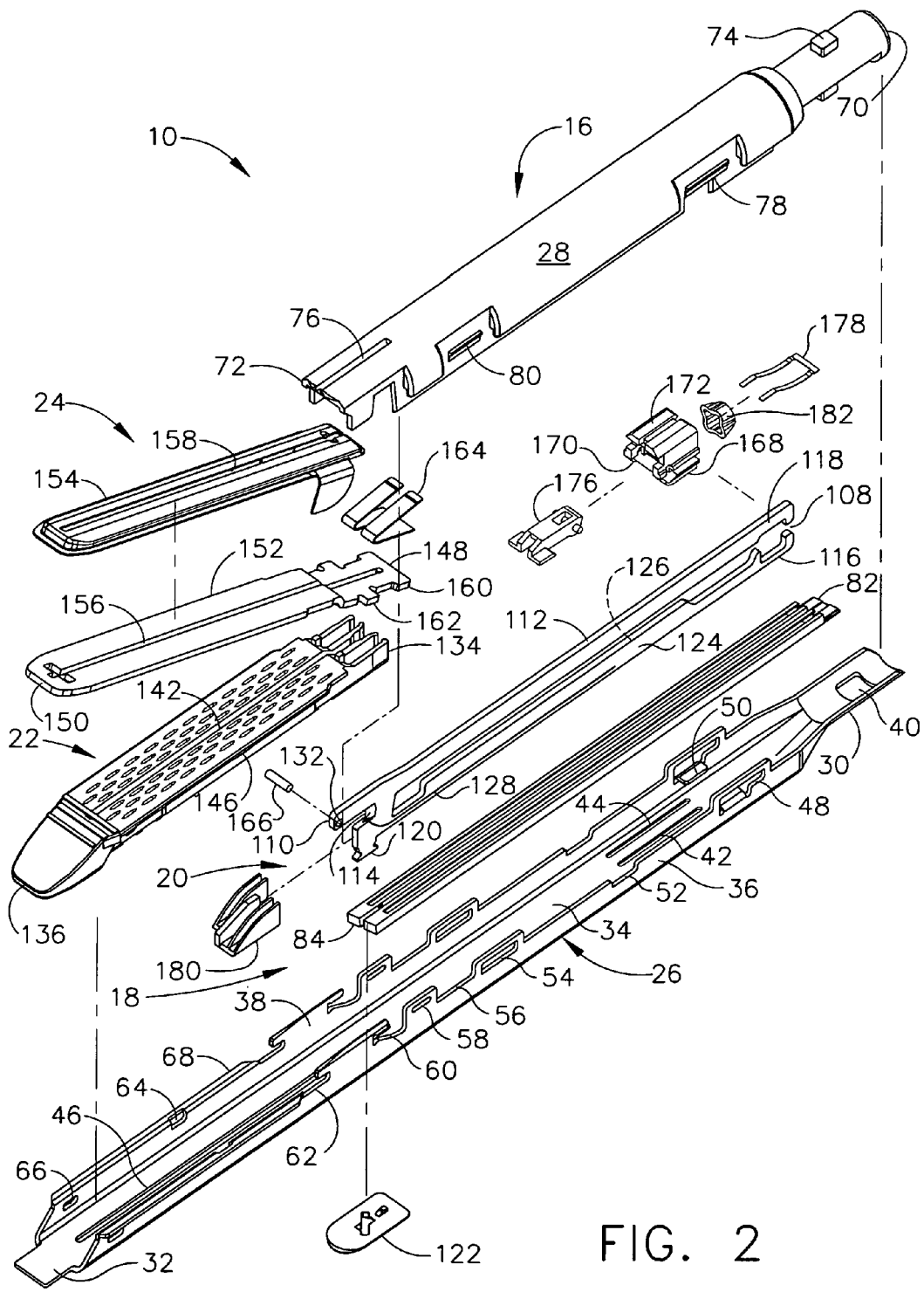

FIGS. 1-2 illustrate various embodiments of a disposable loading unit 10, with FIG. 2 showing an exploded view of the disposable loading unit 10. The disposable loading unit 10 includes a first end 12 configured for releasable connection to a surgical instrument (see FIG. 15), and a second end 14 opposite the first end 12. The disposable loading unit 10 comprises a housing assembly 16, an agent cartridge 18, a knife assembly 20, a staple cartridge 22, and an anvil assembly 24. The disposable loading unit 10 may be removed and discarded after a single use.

The housing assembly 16 comprises a channel 26 and a channel cover 28 connected to the channel 26. The channel 26 and the channel cover 28 may be fabricated from any suitable material such as, for example, a plastic. The channel 26 includes a first end 30 proximate the first end 12 of the disposable loading unit 10 and a second end 32 proximate the second end 14 of the disposable loading unit 10. The channel 26 comprises a base 34, a first wall 36, and a second wall 38. According to various embodiments, the base 34 defines an opening 40 proximate the first end 30 of the channel 26, a first slot 42 proximate the first end 30 of the channel 26, a second slot 44 proximate the first end 30 of the channel 26, and a third slot 46 proximate the second end 32 of the channel. The first wall 36 is connected to the base 34 and extends generally perpendicular therefrom. The second wall 38 is connected to the base 34, extends generally perpendicular therefrom, and is opposite the first wall 36. The second wall 38 may be a mirror-image of the first wall 36, and the first and second walls 36, 38 may be fabricated integral with the base 34. According to various embodiments, each of the first and second walls 36, 38 define a fourth slot 48, a first tab 50, a first indent 52, a fifth slot 54, a second indent 56, a sixth slot 58, a third indent 60, a fourth indent 62, a seventh slot 64, an eighth slot 66, and a first flange 68.

The channel cover 28 includes a first end 70 proximate the first end 12 of the disposable loading unit 10 and a second end 72 opposite the first end 70, and may be symmetric along an axis that extends from the first end 70 of the channel cover 28 to the second end 72 of the channel cover 28. The channel cover 28 is configured to engage with the channel 26 at a plurality of locations. According to various embodiments, the channel cover 28 defines a pair of coupling pegs 74 proximate the first end 70 of the channel cover 28 that extends from the channel cover 28. One of the coupling pegs 74 passes through the opening 40 defined by the channel 26. The channel cover 28 also defines a slit 76 proximate the second end 72 of the channel cover 28. According to various embodiments, the channel cover 28 defines a first pair of tabs 78 that pass through and engage with the fourth slots 48, a first pair of interior projections that mate with the first indents 52, a second pair of tabs 80 that pass through and engage with the fifth slots 54, a second pair of interior projections that mate with the second indents 56, and a third pair of interior projections that engage with the sixth slots 58. According to other embodiments, the channel 26 and the channel cover 28 may be fabricated to include other arrangements of tabs, slots, projections, indents, etc. that may be utilized to connect the channel cover 28 to the channel 26.

The agent cartridge 18 is connected to the housing assembly 16 and houses at least one medical agent. The medical agent may be any type of medical agent. For example, the medical agent may comprise an anesthetic, an adhesive, an antibiotic, a cauterizing substance, a coagulant, a growth hormone, a hemostatic agent, a sealant, etc., or any combination thereof.

Figure 3:
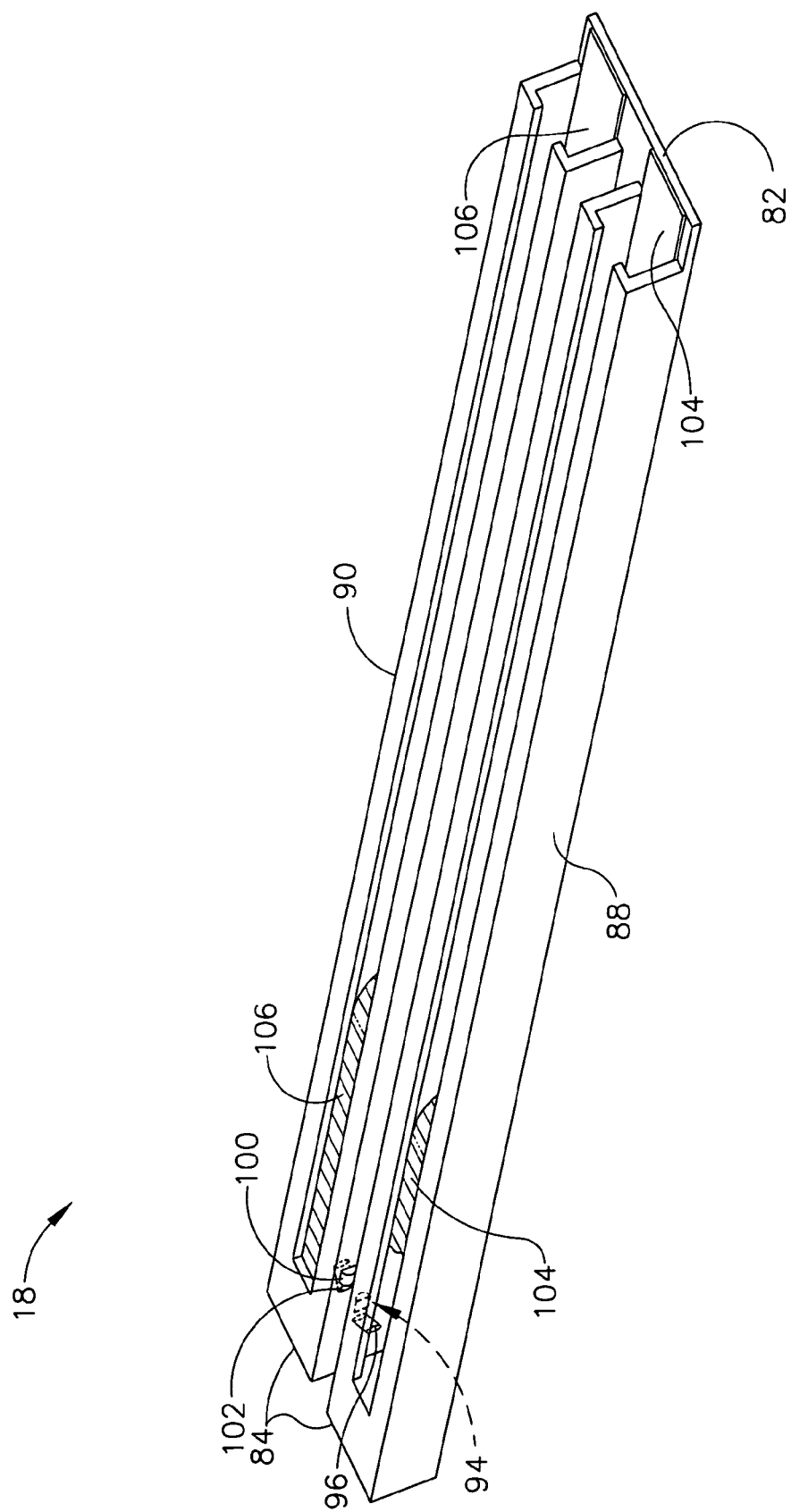
FIG. 3 illustrates various embodiments of an agent cartridge.

The agent cartridge 18 includes a first end 82 proximate the first end 12 of the disposable loading unit 10 and a second end 84 opposite the first end 82. The agent cartridge 18 comprises a body 86 (see FIG. 6) that may be fabricated from any suitable material (e.g., a plastic) that is compatible with the medical agent. According to various embodiments, the body 86 comprises a first section 88 and a second section 90. The first section 88 may define a first spline that extends therefrom, and passes through and engages with the first slot 42 of the base 34 of the channel 26. As shown in FIG. 3, the first section 88 may also define a first projection 94 and a first dispensing port 96 proximate the second end 84 of the agent cartridge 18. The first projection 94 may be of any shape (e.g., rectangular, triangular, hemispherical, etc.). The first dispensing port 96 is positioned between the first projection 94 and the second end 84 of the agent cartridge 18. The second section 90 is spaced apart from the first section 88 and may be a mirror-image thereof. The second section 90 may define a second spline that extends therefrom, and passes through and engages with the second slot 44 of the base 34 of the channel 26. As shown in FIG. 3, the second section 90 may define a second projection 100 and a second dispensing port 102 proximate the second end 84 of the agent cartridge 18. The second projection 100 may be of any shape (e.g., rectangular, triangular, hemispherical, etc.). The second dispensing port 102 is positioned between the second projection 100 and the second end 84 of the agent cartridge 18. According to other embodiments, the body 86 may be fabricated to include other arrangements of splines, tabs, fasteners, etc. that may be utilized to connect the agent cartridge 18 to the housing assembly 16.

According to various embodiments, the agent cartridge 18 also comprises a first sealing member 104 (see FIG. 3) and a second sealing member 106 (see FIG. 3). The first sealing member 104 is connected to the first section 88 and cooperates with the first section 88 to house a medical agent. Similarly, the second sealing member 106 is connected to the second section 90 and cooperates with the second section 90 to house a second medical agent. The first medical agent may be the same or different than the second medical agent.

The knife assembly 20 is connected to the housing assembly 16, and includes a first end 108 proximate the first end 12 of the disposable loading unit 10 and a second end 110 opposite the first end 108. The knife assembly 20 comprises a body 112 and a cutting surface 114. According to various embodiments, the cutting surface 114 comprises a portion of a knife blade that is connected to the body 112 proximate the second end 110 of the knife assembly 20. The body 112 may be fabricated from any suitable material such as, for example, a plastic. According to various embodiments, the body 112 comprises a first clamping member 116 proximate the first end 108 of the knife assembly 20, a second clamping member 118 proximate the first end 108 of the knife assembly 20, and a foot member 120 proximate the second end 110 of the knife assembly 20. The foot member 120 passes through the third slot 46 of the base 34 of the channel 26 and is mated with a retainer 122 that is external to the housing assembly 16 and serves to slidably connect the body 112 to the housing assembly 16 such that the knife assembly 20 can be selectively advanced along the third slot 46 toward the second end 32 of the channel 26.

The body 112 of the knife assembly 20 also comprises a first surface 124 and a second surface 126 (see FIG. 6) that is opposite the first surface 124. The first surface 124 of the body 112 is adjacent the first section 88 of the agent cartridge 18, and the second surface 126 of the body 112 is adjacent the second section 90 of the agent cartridge 18. The first surface 124 of the body 112 defines a first groove 128 and the second surface 126 of the body 112 defines a second groove 130 (see FIG. 6). The first groove 128 is proximate the cutting surface 114 of the knife assembly 20 and may extend any distance along the first surface 124 of the body 112 toward the first end 108 of the knife assembly 20. The first groove 128 is adjacent the first dispensing port 96 and is configured to receive the first projection 94 of the first section 88 of the body 86. The second groove 130 is proximate the cutting surface 114 of the knife assembly 20 and may extend any distance along the second surface 126 of the body 112 toward the first end 108 of the knife assembly 20. The second groove 130 is adjacent the second dispensing port 102 and is configured to receive the second projection 100 of the second section 90 of the body 86. Each of the first and second grooves 128, 130 may be of any shape (e.g., rectangular, triangular, hemispherical, etc.) suitable for respectively receiving the first projection 94 and the second projection 100. The body 112 of the knife assembly 20 may also define an opening 132 that extends from the first surface 124 to the second surface 126 proximate the second end 110 of the knife assembly 20.

The staple cartridge 22 is connected to the housing assembly 16. The staple cartridge 22 includes a first end 134 and a second end 136 opposite the first end 134. The second end 136 of the staple cartridge 22 is proximate the second end 14 of the disposable loading unit 10. The staple cartridge 22 may be similar to other staple cartridges known in the art. For example, the staple cartridge 22 may comprise a plurality of surgical fasteners and a plurality of corresponding pushers. According to various embodiments, the staple cartridge 22 defines a slot 142 that is aligned with the third slot 46 of the base 34 of the channel 26 and extends from the first end 134 of the staple cartridge 22 toward the second end 136 of the staple cartridge 22. The staple cartridge 22 may also define tabs that extend from the staple cartridge 22 and pass through and engage with the seventh slots 64 and the eighth slots 66 of the channel 26, and may further comprise flanges 146 which frictionally engage the first and second walls 36, 38 of the channel 26 proximate the second end 32 of the channel 26. According to other embodiments, the staple cartridge 22 may be fabricated to include other arrangements of tabs, flanges, fasteners, etc. that may be utilized to connect the staple cartridge 22 to the housing assembly 16.

The anvil assembly 24 is connected to the housing assembly 16. The anvil assembly 24 includes a first end 148 and a second end 150 opposite the first end 148. The second end 150 of the anvil assembly 24 is proximate the second end 14 of the disposable loading unit 10. The anvil assembly 24 may be similar to other anvil assemblies known in the art. For example, the anvil assembly 24 is moveable between an open position and a closed position, and may comprise an anvil plate 152 and an anvil body 154 connected to the anvil plate 152. According to various embodiments, the anvil plate 152 defines a slot 156 that is aligned with the slot 142 of the staple cartridge 22, and the anvil body 154 defines a slot 158 that is aligned with the slot 156 of the anvil plate 152. The anvil plate 152 may also define a first pair of ears 160 proximate the first end 148 of the anvil assembly 24 and a second pair of ears 162 positioned between the first pair of ears 160 and the second end 150 of the anvil assembly 24. One of the ears of the second pair of ears 162 is engaged with the third indent 60 defined by the first wall 36 of the channel 26, and the other ear of the second pair of ears 162 is engaged with the third indent 60 defined by the second wall 38 of the channel 26. A spring member 164 or other biasing arrangement may be utilized to urge the anvil assembly 24 to the open position, and an anvil pin 166 that passes through the opening 132 of the knife assembly 20 may be utilized to urge the anvil assembly 24 toward the closed position. According to other embodiments, the anvil assembly 24 may be fabricated to include other fastener arrangements that may be utilized to connect the anvil assembly 24 to the housing assembly 16.

The disposable loading unit 10 may further comprise a first medical agent driver 168 proximate the first end 82 of the agent cartridge 18 and a second medical agent driver 170 (see FIG. 6) proximate the first end 82 of the agent cartridge 18. According to various embodiments, the first and second medical agent drivers 168, 170 may comprise a portion of a drive block 172 that is coupled to the knife assembly 20 at the first end 108 thereof. For such embodiments, the first medical agent driver 168 may be configured to slidably fit within the first section 88 of the body 86 of the agent cartridge 18, and the second medical agent driver 170 may be configured to slidably fit within the second section 90 of the body 86 of the agent cartridge 18. According to other embodiments, the first medical agent driver 168 may comprise an electrically activated polymer that is in contact with the first section 88 of the body 86 of the agent cartridge 18 as shown in FIGS. 13 and 14. Similarly, the second medical agent driver 170 may comprise an electrically activated polymer that is in contact with the second section 90 of the body 86 of the agent cartridge 18. For such embodiments, each of the first and second medical agent drivers 168, 170 may be electrically connected to a contact 174 (see FIG. 14) that is proximate the first end 12 of the disposable loading unit 10 and is connected to a voltage source.

As shown in FIG. 2, the disposable loading unit 10 may also comprise a lock member 176 connected to the drive block 172, a retainer 178 for coupling the lock member 176 to the drive block 172, and a sled 180 positioned proximate the second end 110 of the knife assembly 20. The drive block 172, the lock member 176, the retainer 178 and the sled 180 may be similar to those known in the art. The disposable loading unit 10 may further comprise a firing member adapter 182 connected to the drive block 172. The firing member adapter 182 is configured for receiving a firing member that does not comprise a portion of the disposable loading unit 10.

Figures 4, 5:
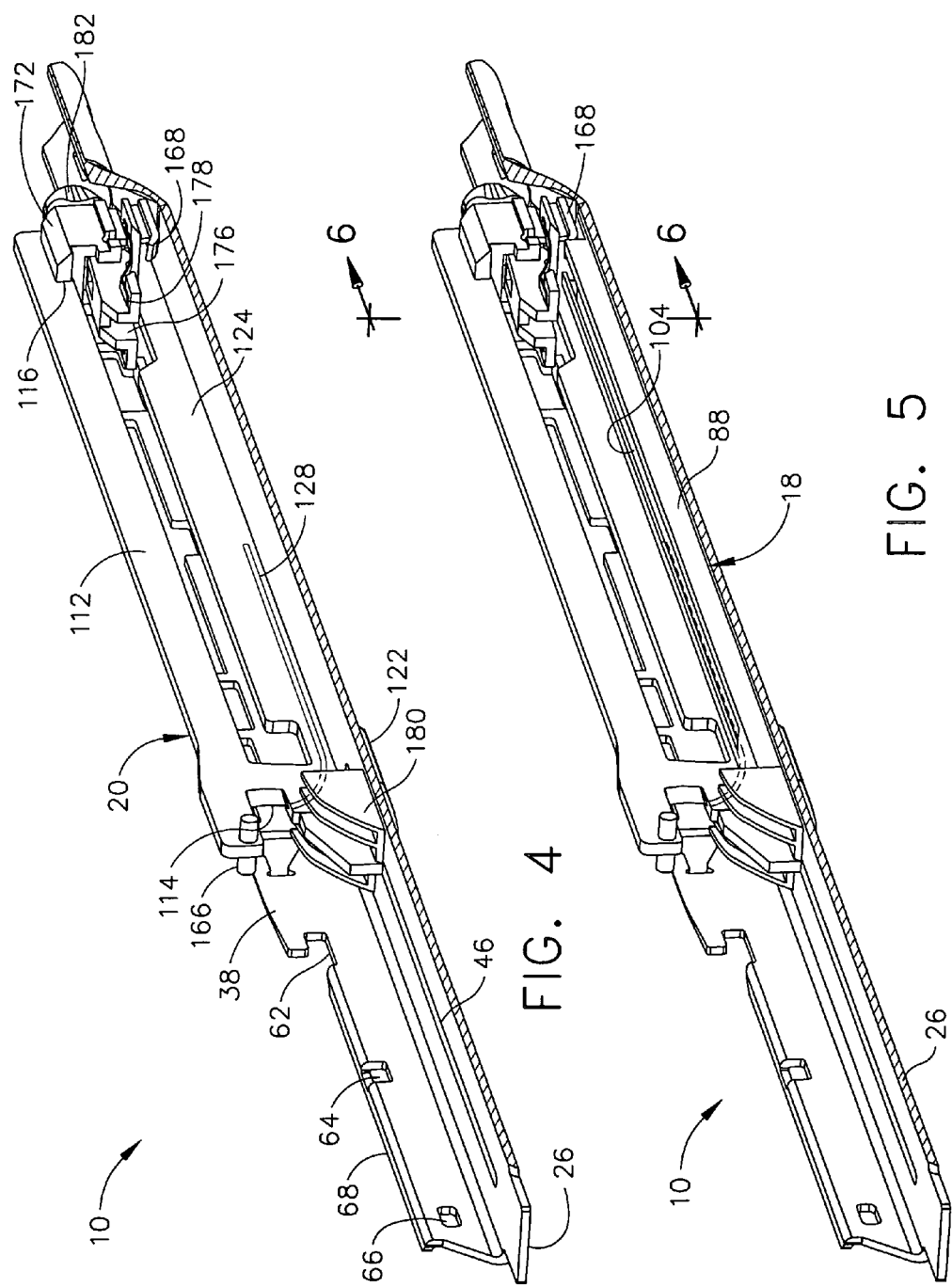
FIG. 4 illustrates various embodiments of a disposable loading unit.
FIG. 5 illustrates various embodiments of a disposable loading unit.

FIG. 4 illustrates various embodiments of the disposable loading unit 10. For purposes of clarity only, certain portions of the disposable loading unit 10 are not shown in this figure. The first and second clamping members 116, 118 are connected to the drive block 172, and the lock member 176 and the retainer 178 are also connected to the drive block 172. The first medical agent driver 168 is connected to the drive block 172, and the sled 180 is proximate the second end 110 of the knife assembly 20. The general positions of the shown components relative to the channel 26 represent the positions of the components prior to the advancement of the firing member (i.e., the pre-fire positions).

FIG. 5 illustrates various embodiments of the disposable loading unit 10. For purposes of clarity only, certain portions of the disposable loading unit 10 are not shown in this figure. FIG. 5 is similar to FIG. 4, and shows that the first medical agent driver 168 is aligned with the first section 88 of the body 86 of the agent cartridge 18. The general positions of the shown components relative to the channel 26 represent the positions of the components prior to the advancement of the firing member (i.e., the pre-fire positions).

Figure 6:
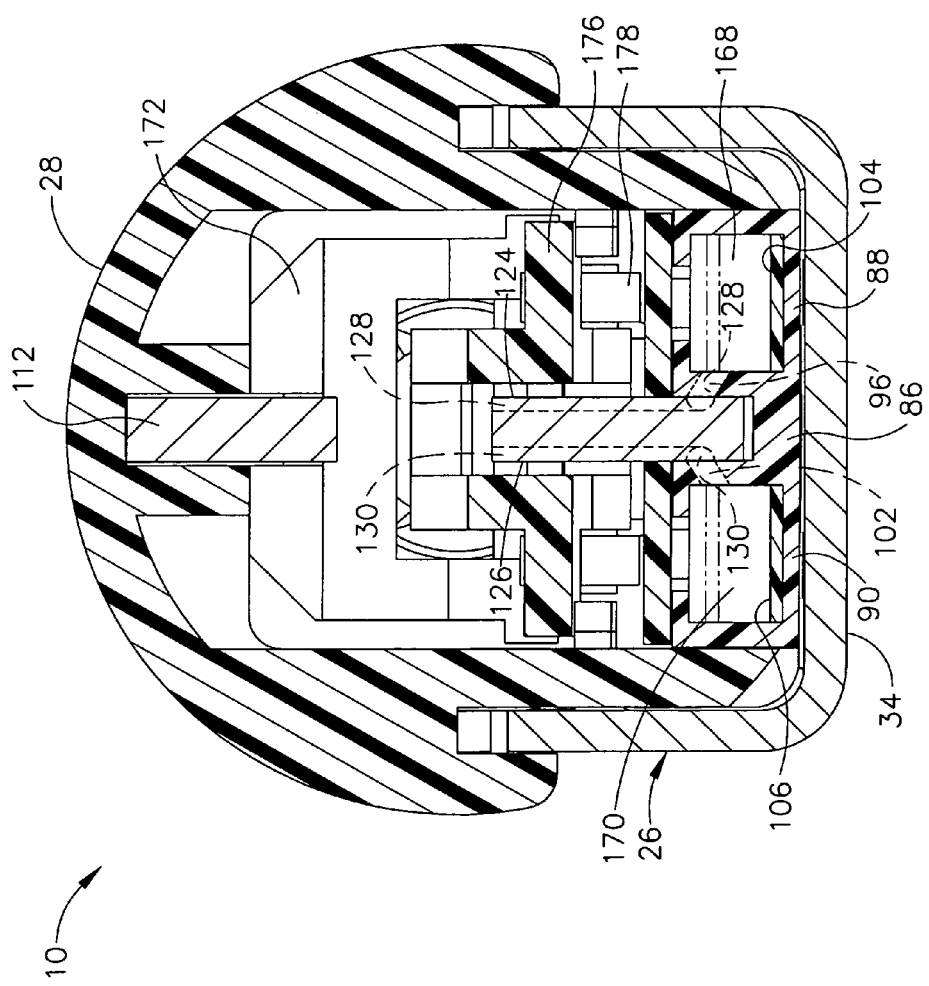
FIG. 6 illustrates various embodiments of a disposable loading unit.

FIG. 6 illustrates various embodiments of the disposable loading unit 10, and shows a cross-section of the disposable loading unit 10 along line 6-6 of FIG. 5. As shown in FIG. 6, the first and second dispensing ports 96, 102 may pass through the respective first and second sections 88, 90 at an angle relative to the base 34 of the channel 26.

Figure 7:
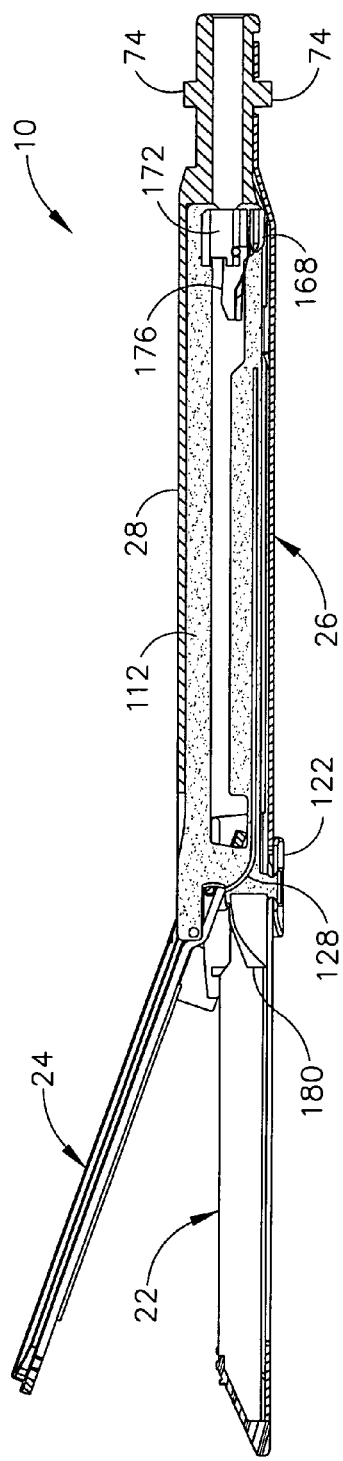
FIG. 7 illustrates various embodiments of a disposable loading unit.

FIG. 7 illustrates various embodiments of the disposable loading unit 10. For purposes of clarity only, certain portions of the disposable loading unit 10 are not shown in this figure. The anvil assembly 24 is shown in the open position relative to the staple cartridge 22 in FIG. 7. The general positions of the shown components relative to the channel 26 represent the positions of the components prior to the advancement of the firing member (i.e., the pre-fire positions).

Figure 8:
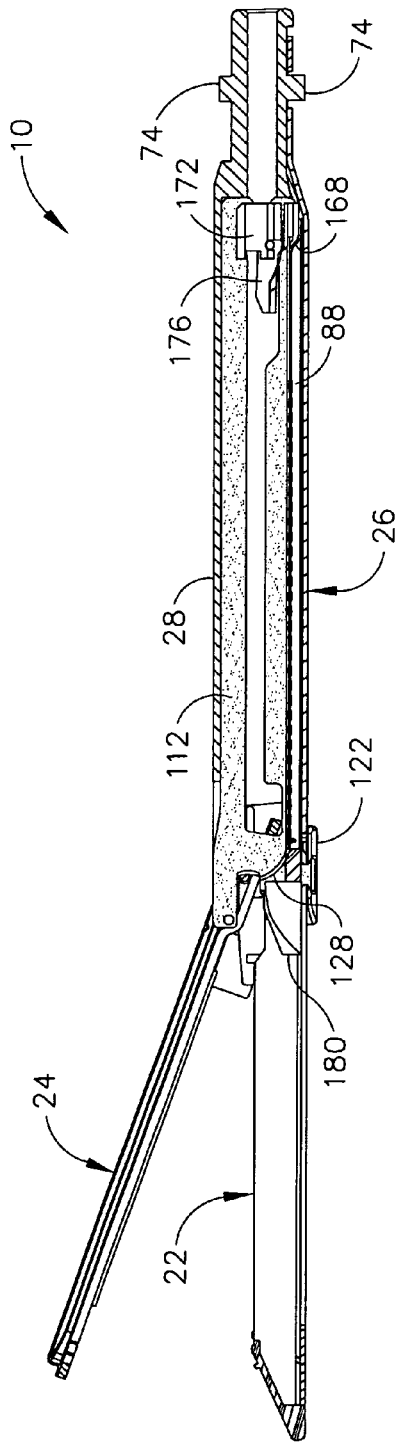
FIG. 8 illustrates various embodiments of a disposable loading unit.

FIG. 8 illustrates various embodiments of the disposable loading unit 10. For purposes of clarity only, certain portions of the disposable loading unit 10 are not shown in this figure. FIG. 8 is similar to FIG. 7, but also shows the first section 88 of the body 86 of the agent cartridge 18.

FIG. 9 illustrates various embodiments of the disposable loading unit 10, and is an enlarged version of a portion of the disposable loading unit 10 illustrated in FIG. 8.

FIG. 10 illustrates various embodiments of the disposable loading unit 10, and is an enlarged version of a portion of the disposable loading unit 10 illustrated in FIG. 8.

FIG. 11 illustrates various embodiments of the disposable loading unit 10. For purposes of clarity only, certain portions of the disposable loading unit 10 are not shown in this figure. The general positions of the shown components relative to the channel 26 represent the positions of the components after the advancement of the firing member (i.e., the post-fire positions). As shown in FIG. 11, the anvil assembly 24 is in the closed position, and the post- fire positions of the knife assembly 20, the anvil assembly 24, the first medical agent driver 168, the drive block 172, and the lock member 176 are different than their pre-fire positions relative to the channel 26.

FIG. 12 illustrates various embodiments of the disposable loading unit 10, and is an enlarged version of a portion of the disposable loading unit 10 illustrated in FIG. 11. As shown in FIG. 12, the post-fire position of the first medical agent driver 168 may be some distance from the first dispensing port 96. Similarly, the post-fire position of the second medical agent driver 170 may be some distance from the second dispensing port 102.

FIG. 13 illustrates various embodiments of the disposable loading unit 10. For purposes of clarity only, certain portions of the disposable loading unit 10 are not shown in this figure. FIG. 13 is similar to FIG. 4, but shows the first section 88 of the body 86 of the agent cartridge 18, and also shows the first medical agent driver 168 embodied as an electrically activated polymer. FIG. 13 also illustrates the conductors 184 that electrically connect the first medical agent driver 168 and the contact 174. The general positions of the shown components relative to the channel 26 represent the positions of the components prior to the advancement of the firing member (i.e., the pre-fire positions).

FIG. 14 illustrates various embodiments of the disposable loading unit 10. For purposes of clarity only, certain portions of the disposable loading unit 10 are not shown in this figure. FIG. 14 is similar to FIG. 8, but shows the first medical agent driver 168 embodied as an electrically activated polymer. FIG. 14 also illustrates the contact 174 and the conductors 184 that electrically connect the contact 174 and the first medical agent driver 168. The general positions of the shown components relative to the channel 26 represent the positions of the components prior to the advancement of the firing member (i.e., the pre-fire positions).

FIG. 15 illustrates various embodiments of a surgical instrument 200. The surgical instrument 200 includes a handle assembly 202, an elongated body 204 connected to the handle assembly 202, and a disposable loading unit 10 releasably connected to the elongated body 204. The disposable loading unit 10 may be releasably connected to the elongated body 204 in any manner. For example, the disposable loading unit 10 may be releasably connected to the elongated body 204 via the coupling pegs 74 described hereinabove. The handle assembly 202 and the elongated body 204 may be similar to other handle assemblies and elongated bodies known in the art. For example, the handle assembly 202 may include means for advancing a firing member that is surrounded by the elongated body 204 and is utilized to advance the drive block 172 of the disposable loading unit 10.

In operation, when the firing member is advanced, the advancement of the firing member causes the drive block 172 to advance toward the second end 14 of the disposable loading unit 10. As the drive block 172 advances, the knife assembly 20 advances toward the second end 14 of the disposable loading unit 10. The advancement of the knife assembly 20 causes the anvil pin 166 to cooperate with the anvil body 154 to urge the anvil assembly 24 toward the closed position. The advancement of the knife assembly 20 also causes the sled 180 to advance toward the second end 14 of the disposable loading unit 10. As the sled 180 advances, the angled leading edges of the sled 180 sequentially contact pushers supported within the staple cartridge 22, causing the pushers to urge surgical fasteners from the staple cartridge 22 in a known manner.

For embodiments where the first and second medical agent drivers 168, 170 are coupled to the knife assembly 20, the advancement of the drive block 172 advances the first and second medical agent drivers 168, 170 within the first and second sections 88, 90 of the body 86 toward the second end 84 of the agent cartridge 18. As the first and second medical agent drivers 168, 170 advance, they make contact with the first and second sealing members 104, 106 and urge the first and second medical agents out of the first and second dispensing ports 96, 102. Because the post-fire positions of the first and second medical agent drivers 168, 170 may be some distance from the first and second dispensing ports 96, 102, some medical agent may still remain housed by the agent cartridge 18 after the first and second medical agent drivers 168, 170 advance from their pre-fire positions to their post-fire positions.

For embodiments where the first and second medical agent drivers 168, 170 are electrically activated polymers, the advancement of the firing member causes an electrical connection to be made with the contact 174, causing a voltage to be applied to the first and second medical agent drivers 168, 170. In response to the applied voltage, the first and second medical agent drivers 168, 170 expand within the first and second sections 88, 90 of the body 86 of the agent cartridge 18 and urge the first and second medical agents out of the first and second dispensing ports 96, 102.

With the first projection 94 and the second projection 100 serving as stops which restrict the flow of the first and second medical agents along the grooves 128, 130 in the direction toward the first end 12 of the disposable loading unit 10, the medical agents urged out of the first and second dispensing ports 96, 102 advance along the respective grooves 128, 130 toward the cutting surface 114 of the disposable loading unit 10. As the knife assembly 20 advances along the slot 142 defined by the staple cartridge 22, the staple cartridge 22 also serves to keep the medical agents in the grooves 128, 130 until the medical agents exit the grooves 128, 130 proximate the cutting surface 114. The medical agents are thus effectively delivered to the site of the cutting and stapling.

After a single use, the disposable loading unit 10 is removed from the elongated body 204 and may be replaced with another disposable loading unit 10 for another use. This process may be repeated any number of times. Therefore, the handle assembly 202 and the elongated body 204 connected thereto may be reused any number of times.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

What is claimed is:

1. A disposable loading unit, comprising:
   a housing assembly;
   a knife assembly connected to the housing assembly; and
   an agent cartridge connected to the housing assembly, wherein the agent cartridge houses a medical agent, and wherein the disposable loading unit is configured to deliver the medical agent proximate a cutting surface of the knife assembly; and
   at least one medical agent driver in contact with the agent cartridge, wherein the at least one medical agent driver comprises an electrically activated polymer.

2. The disposable loading unit of claim 1, wherein the knife assembly comprises a first surface that defines a first groove proximate the cutting surface, wherein the first groove is in fluid communication with the agent cartridge, and wherein the first groove is configured to deliver the medical agent from the agent cartridge proximate to the cutting surface.

3. The disposable loading unit of claim 2, wherein the knife assembly further comprises a second surface opposite the first surface, wherein the second surface defines a second groove proximate the cutting surface, wherein the second groove is in fluid communication with the agent cartridge, and wherein the second groove is configured to deliver the medical agent from the agent cartridge proximate to the cutting surface.

4. The disposable loading unit of claim 2, wherein the agent cartridge comprises:
   a body; and
   a first dispensing port defined by the body, wherein the first dispensing port is in fluid communication with the first groove.

5. The disposable loading unit of claim 4, wherein the knife assembly further comprises a second surface that defines a second groove proximate the cutting surface, and wherein the body further defines a second dispensing port in fluid communication with the second groove.

6. The disposable loading unit of claim 4, wherein the agent cartridge further comprises a first cavity configured to house the medical agent therein, and wherein the first cavity is at least partially defined by a first sealing member connected to the body.

7. The disposable loading unit of claim 6, wherein the agent cartridge further comprises a second cavity configured to house the medical agent therein, and wherein the second cavity is at least partially defined by a second sealing member connected to the body.

8. The disposable loading unit of claim 1, further comprising:
   a staple cartridge connected to the housing assembly; and
   an anvil assembly connected to the housing assembly.

9. The disposable loading unit of claim 1, further comprising at least one conductor configured to place the electrically activated polymer in electrical communication with a voltage source.

10. The disposable loading unit of claim 1, wherein the medical agent driver is expandable to dispense the medical agent from the agent cartridge when placed in electrical communication with a voltage source.

11. A surgical instrument, comprising:
    a handle assembly;
    an elongated body connected to the handle assembly; and
    a disposable loading unit releasably connected to the elongated body, wherein the disposable loading unit comprises:
       a housing assembly;
       a knife assembly connected to the housing assembly;
       an agent cartridge connected to the housing assembly, wherein the agent cartridge houses a medical agent; and
       at least one medical agent driver in contact with the agent cartridge, wherein the at least one medical agent driver comprises an electrically activated polymer, and wherein the disposable loading unit is configured to deliver the medical agent proximate a cutting surface of the knife assembly.

12. The surgical instrument of claim 11, wherein the knife assembly comprises at least one surface that defines a groove proximate the cutting surface, wherein the groove is in fluid communication with the agent cartridge, and wherein the groove is configured to deliver the medical agent from the agent cartridge proximate to the cutting surface.

13. The surgical instrument of claim 12, wherein the agent cartridge comprises:
    a body; and
    at least one dispensing port defined by the body, wherein the at least one dispensing port is in fluid communication with the groove.

14. The surgical instrument of claim 11, further comprising:
    a staple cartridge connected to the housing assembly; and
    an anvil assembly connected to the housing assembly.

15. The surgical instrument of claim 11, further comprising at least one conductor configured to place the electrically activated polymer in electrical communication with a voltage source.

16. The surgical instrument of claim 11, wherein the electrically activated polymer is expandable to dispense the medical agent from the agent cartridge when placed in electrical communication with a voltage source.

17. An assembly for a surgical instrument, comprising:
    a housing;
    a cutting member relatively movable with respect to the housing, the cutting member having a cutting surface;

an agent cartridge connected to the housing, wherein the agent cartridge includes a cavity configured to house a medical agent therein; and a driver engaged with the agent cartridge to dispense the medical agent from the agent cartridge, wherein the driver comprises an electrically activatable polymer.

18. The assembly of claim 17, wherein the surgical instrument comprises a handle and an elongate body extending from the handle, and wherein the assembly is configured to be releasably connected to the elongate body.

19. The assembly of claim 17, wherein the agent cartridge is directly connected to the housing.

20. The assembly of claim 17, wherein the cutting member includes a groove proximate the cutting surface, wherein the groove is in fluid communication with the cavity of the agent cartridge, and wherein the groove is configured to deliver the medical agent from the cavity proximate to the cutting surface.

21. The assembly of claim 20, wherein the agent cartridge comprises a body and at least one dispensing port defined by the body, and wherein the at least one dispensing port is in fluid communication with the cavity and the groove.

22. The assembly of claim 17, further comprising a staple cartridge connected to the housing.

23. The assembly of claim 17, further comprising at least one conductor configured to place the electrically activatable polymer in electrical communication with a voltage source.

24. The assembly of claim 17, wherein the electrically activatable polymer is expandable to dispense the medical agent from the agent cartridge when placed in electrical communication with a voltage source.

* * * * *